United States Patent [19]

Rosen

[11] Patent Number: 4,572,831
[45] Date of Patent: Feb. 25, 1986

[54] SKIN-MARKING COMPOSITIONS AND DEVICES, AND THEIR USE

[76] Inventor: Gerald M. Rosen, 403 Knob Ct., Chapel Hill, N.C. 27514

[21] Appl. No.: 435,152

[22] Filed: Oct. 19, 1982

[51] Int. Cl.⁴ .................... A61K 49/00; G01N 31/00; G01N 31/22
[52] U.S. Cl. ........................ 424/7.1; 424/9; 436/86; 436/90; 436/172; 514/453
[58] Field of Search .................... 424/7.1, 9; 436/172, 436/86, 90; 514/453

[56] References Cited

U.S. PATENT DOCUMENTS

| | | | |
|---|---|---|---|
| 3,640,889 | 2/1972 | Stewart | 424/9 |
| 3,812,181 | 3/1974 | Leimgruber et al. | 436/86 |
| 3,830,629 | 8/1974 | Leimgruber et al. | 436/90 |
| 3,871,825 | 3/1974 | Leimgruber et al. | 436/86 |
| 3,969,373 | 7/1976 | Cleeland et al. | 436/172 |
| 4,045,487 | 8/1977 | Cleeland et al. | 436/172 |

*Primary Examiner*—Christine M. Nucker
*Attorney, Agent, or Firm*—Millen & White

[57] ABSTRACT

Fluorescamine or like compounds react with the epidermis when applied to the skin and form, within about 15 to 30 minutes after application to the skin, a long-lasting reaction product, which is invisible in ordinary light but which fluoresces intensely under ultraviolet light. Such markings resist removal by abrasion and repeated washings. Organic solutions of such compounds, preferably containing a fugitive dyestuff or pigment and used as the marking fluid of a conventional felt-tipped pen, can be used to mark skin for radiological or diagnostic purposes. Inanimate objects can be coated with these compounds to detect human contact therewith.

4 Claims, 3 Drawing Figures

SKIN-MARKING COMPOSITIONS AND DEVICES, AND THEIR USE

BACKGROUND OF THE INVENTION

1. Field of the Invention

This invention relates to novel skin-marking compositions, to their use to render skin fluorescent under ultraviolet light and to marking devices comprising them.

2. Description of the Related Art

The use of skin-marking compositions to delineate boundaries of bodily areas requiring medical therapy, such as for radiation treatment of cancer, to identify areas contacted with allergens, to monitor the status of ring worm and other skin infections, and for other dermatological purposes, is conventional. Typically, visible compounds, such as bright purple or green dyes or inks, have been used. See, for example, U.S. Pat. No. 3,551,554. Although adequate for marking purposes, a visible dye has an adverse psychological impact on a patient so marked, because of the dye's conspicuous visibility during a typically prolonged course of radiation or other therapy.

To avoid this problem, U.S. Pat. No. 3,640,889 utilizes skin-marking compositions that contain a fluorescent dyestuff which becomes visible only under ultraviolet light. Thus, at the times prescribed for treatment, the site so marked can be perceived by the therapist upon illumination of the marked area with ultraviolet light.

To render its marking composition more permanent, the '889 patent incorporates a polyvinyl acetate compound into its marking composition to provide a coating layer on the surface of the skin to entrap dye molecules and render the composition resistant to washing and normal abrasion, thereby extending the time period during which the dye remains on the skin and can be observed. However, such a vinyl layer is physically uncomfortable for a patient so treated. The coating may also inhibit the normal sloughing of surface skin layers, as well as the perspiratory and other natural functions of the skin. Moreover, the compositions can still be removed by washing, thereby necessitating repeated applications of dye during the course of therapy. Such reapplication is disadvantageous in that it inefficiently consumes the valuable time of medical professionals and introduces the opportunity for inaccurately or erroneously remarking therapy area boundaries.

The use of fluorescent dyestuffs to temporarily mark skin is well known; for example, in allergy diagnosis to delineate areas of the skin to which various allergens are applied and to identify customers who have paid admission in amusement areas. Such dyestuffs are readily removed by washing.

Florescamine (4-phenylspiro[furan-2(3H),1'-phthalanl]-3,3'- dione) and other structurally related furanones are reagents which, although not fluorescent themselves, are known to react with primary and secondary amines to form a reaction product which is intensely fluorescent under ultraviolet light. They are known as fluorogenic dyes because they become fluorescent only after undergoing a chemical reaction with amino acids. These reagents are used as a rapid and sensitive in vitro assay of amino acids, peptides, proteins and other primary and secondary amines. Such dyes are useful as quantitative, fluorometric indicators because their substrate proteins are present in solution and are readily accessible on all sides. See U.S. Pat. Nos. 3,812,181; 3,830,629; 3,871,825; 3,969,373; 4,045,487; and 4,238,589; which disclosures are incorporated herein by reference. Although the latter patents disclose the furanones as fluorogenic assay reagents for primary and secondary amine-containing compounds generally, including living organisms such as bacteria and tapeworms the patents make no reference to tissues such as skin.

Moreover, one would not expect that they would similarly react with the relatively inaccessible and non-reactive proteins of the skin, because of the barrier layers that affect dye molecules, such as the various protective processes inherent to the skin that resist penetration and absorption of foreign substances. The structure of proteins is a significant factor also. Binding of dye molecules is dependent upon protein geometry and size, and the accessibility of a protein to the dye. Therefore, protein cell surface receptors that are exposed to the surrounding fluid medium of in vitro cell cultures, or the binding proteins that are present upon the external surfaces of cestodes to attach to and ingest dissolved particulate matter, all behave quite differently from the cuticle, the outer horny layer of skin, that functions to resist penetration by foreign substances. This is confirmed by the fact that if skin is contacted with a solution of one of these furanone compounds, there is virtually no evidence of such a fluorescent reaction product being produced for a substantial period of time. Furthermore, even if exposed surface proteins on the skin did bind some molecules of the dye, this would be inadequate for marking purposes because the outermost skin layers are continually lost by washing or abrasion.

Surprising, we have found that if skin is contacted with one of the aforesaid furanones, after about 15 to 30 minutes, a reaction product with the skin is produced which is invisible under ordinary light but which intensely fluoresces under ultraviolet light. Even more surprising, this reaction product is very permanent and resists removal by bathing or showering for the two or three week normal lifetime of epidermis.

Marking compositions that are only visible under ultraviolet light are also useful as a means of identifying those persons who have come into contact with inanimate objects (such as trucks or boats), or living matter (such as shrubs) or substances (such as hazardous wastes or chemical products) which have previously been coated or treated with these compositions. Military and civilian applications of a fluorescent dye for this purpose are discussed in U.S. Pat. No. 4,219,438. However, this reference teaches the necessary concurrent use of a fluorescent dye along with several solvent and resin components to enhance the useful lifetime of the marker. The fluorogenic reagents of the present invention, when used for marking purposes, are advantageous because they do not require a multi-component mixture, and they are effective when painted or sprayed on an object and then allowed to dry. Furthermore, the fluorogenic compositions are effective at significantly lower concentrations than the prior art dyes which do not selectively bond to epidermal proteins. Most important, because they must bind to protein in order to become fluorescent, in most instances their presence cannot be detected by examination of the object coated with, or material containing, these reagents under an ultraviolet lamp.

It is an object of this invention to provide novel skin-marking compositions that react with the skin to form long-lived reaction products that are invisible under ordinary light but are visible under ultraviolet light. It is another object to provide novel applicators and methods for marking skin to render it fluorescent to ultraviolet light. A further object is to provide a novel method for marking inanimate objects so as to permit identification of persons who come into contact with them. Other objects will be apparent to those skilled in the art.

SUMMARY OF THE INVENTION

Figure 1:
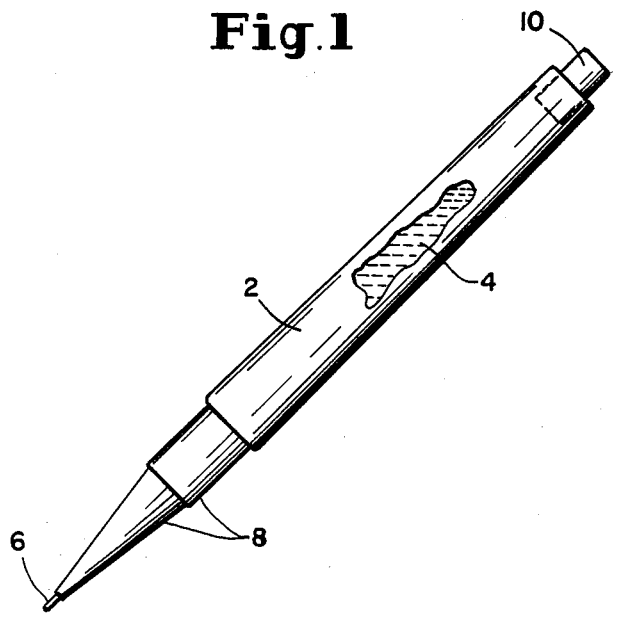
FIG. 1 shows a marking pen containing a fluorogenic skin-marking compound according to this invention, with portions of the pen housing cut away.

In a composition aspect, this invention relates to skin marking compositions adapted for temporarily identifying a defined area of the epidermis under visible light and rendering the area fluorescent for a prolonged period of time under ultraviolet light, comprising a non-fluorescing dermatologically acceptable solution of (a) a fugitive dye or pigment and (b) a skin fluorescingly effective amount of a furanone of the formula

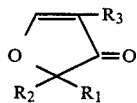

wherein $R_1$ is lower alkoxy or phenyl lower alkoxy and $R_2$ is

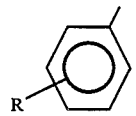

or, $R_1$ and $R_2$ collectively are

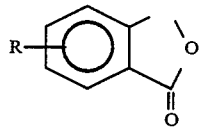

wherein R in each instance is hydrogen or one or more of halogen, lower alkyl, trifluoromethyl, lower alkoxy, nitro, cyano, carboxy or carboxy lower alkyl, and $R_3$ is lower alkyl, phenyl lower alkyl or aryl, in a liquid vehicle in which the furanone compound is stable.

In an article of manufacture aspect, this invention relates to a marking device having a housing, a fluid reservoir in the housing containing a marking fluid, and a marking tip in communication with the fluid in the reservoir, wherein the marking fluid is a non-fluorescing dermatologically acceptable solution of a skin fluorescingly effective amount of a furanone as shown above.

In a first method of use aspect, this invention relates to a diagnostic or therapeutic procedure repeatedly involving a same area of the skin, which occurs at intervals of from 1 to about 21 days and wherein an area of the skin of a patient is marked to delineate the area of the skin involved in the procedure, wherein the skin is marked with a fluorogenically-effective amount of a furanone as shown above, thereby rendering the marked area visible under ultraviolet light and thereafter identifying the marked area by examination of the skin under ultraviolet light, whereby the patient may wash the marked area and avoid the embarassment of visibly marked skin during the time period between procedures.

In a second method of use aspect, this invention relates to a method for indetectably rendering human contact with an inanimate object detectable which comprises applying to a surface of the object, a fluorogenically-effective amount of a furanone of the formula as shown above, thereby rendering the portion of the skin of any person who contacts the thus-treated object fluorescent under ultraviolet light for a period of up to about 21 days.

DETAILED DISCUSSION

The fluorogenic compounds employed in the compositions of this invention are:

(a) non-toxic, that is, substantially free from any significant toxic effects at their effective applied concentration;

(b) substantially free of subjective symptomology, that is, does not itself produce significant symptoms detectable to the person treated;

(c) visible after being applied to the skin only under ultraviolet light and invisible under ordinary white light; and (d) long lasting, that is, once applied they can be observed without frequent reapplications.

The compositions are able to transport a furanone compound as defined herein into and through the outer, horny layer of human epidermis to form an intensely fluorescing reaction product.

The skin-marking reagents employed in the compositions of this invention selectively and covalently bond to the amino groups of cellular or extracellular or fibrous-matrix proteins within the epidermal layers of the skin, and only then fluoresce under ultraviolet light. As used herein, the term "fluorogenic" means that a compound will produce highly fluorescent substances upon reaction with primary or secondary amine-containing compounds to form covalent bonds. An example of such a reagent is fluorescamine (4-phenylspiro[furan-2(3H), 1'-phthalan]-3,3'-dione; FLURAM TM, Hoffmann-LaRoche, Inc.). This furanone compound and others, and their preparations are disclosed in U.S. Pat. Nos. 3,812,181; 3,830,629; 3,871,825; 3,969,373; 4,045,487; and 4,238,589. However, their use, as disclosed in those patents is explicity directed only to in vitro detection of proteins in laboratory solutions, labeling of exposed protein cell-surface markers, or the in vitro labeling of surface proteins of functionally absorptive surfaces such as that of tapeworms.

The carrier fluids for the fluorogenic compounds assist in transporting them into and through the stratum corneum epidermis, or cuticle, which is the outer, horny layer of the epidermis. Although generally they will be in solution in these fluids; suspensions are also effective. Examples of such carrier fluids include simple organic solvents such as ethanol, isopropanol, acetone, ethyl acetate, dimethylformamide, dimethylsulfoxide and mixtures thereof. Other monohydric alkanols (both straight and branched chains) of 1 to 4 carbon atoms are also preferred carrier fluids. Organic solvents such as ketones (for example, acetone) or esters (for example, ethyl acetate) are less preferred because they may tend to irritate human skin. Thus, the preferred carrier fluids will be dermatologically acceptable so as to avoid unwanted irritation. Because the furanones generally are water insoluble, any water in the carrier fluid should be insufficient to render the furanone insoluble therein.

Because it is the carrier fluid's ability to carry a fluorogenic reagent that is necessary to this invention, rather than a particular type or chemical structure of the fluid, it is apparent that many different types or mixtures of such carriers are equivalent to those specifically distinguished. Thus, the viscosity of the carrier fluid may vary widely and its volatility may range from highly volatile to relatively involatile. Fluids of varying degress of penetrating ability may be selected as appropriate for a particular type of skin or medical condition. For coating an object, such as paper money, a relatively more volatile carrier fluid is preferred.

The furanones in the skin-marking compositions of this invention are of the formula

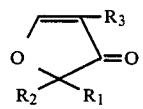

wherein $R_1$ is lower alkoxy or phenyl lower alkoxy and $R_2$ is

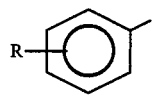

or, $R_1$ and $R_2$ collectively are

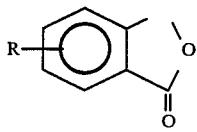

wherein R in each instance is hydrogen or one or more of halogen, lower alkyl, trifluoromethyl, lower alkoxy, nitro, cyano, carboxy or carboxy lower alkyl, and $R_3$ is lower alkyl, phenyl lower alkyl or aryl.

In the general furanone formula shown above, lower alkyl includes both straight and branched chain alkyl containing up to and including eight carbon atoms; lower alkoxy is a lower alkyl defined above linked by an ether oxygen atom; aryl includes both carbocyclic and heterocyclic (that is, containing one or more O, S and N atoms as ring members) aromatic ring systems, which may be substituted, for example with one or more of halogen, fluorine, chlorine, bromine or iodine, trifluoromethyl, lower alkyl, lower alkoxy, lower alkanoyloxy, carbonyloxyalkyl, nitro, and cyano. Illustrative aromatic ring systems are phenyl, napthyl, furyl, thienyl, pyrrolyl, imidazolyl, pyridyl, pyrimidinyl, indolyl, quinolyl, oxazolyl, and isoxazolyl. Examples of lower alkoxy groups are methoxy, ethoxy, n-propoxy, n-butoxy, isopropoxy, tert-butoxy, and so forth.

Preferred furanones are those wherein $R_1$ is lower alkyl, $R_2$ is lower phenyl, and $R_3$ is phenyl or phenyl substituted by carboxy or carboxy lower alkyl. Particularly preferred compounds are the compounds wherein $R_1$ is methyl and $R_2$ and $R_3$ are phenyl, that is, 2-methoxy-2,4-diphenyl-3(2H)-furanone; $R_1$ is methyl, $R_2$ is phenyl and $R_3$ is 4-carboxy-phenyl, that is, 2-methoxy-2-phenyl-4(4-carboxy-phenyl)-3(2H)-furanone; and $R_1$ is methyl, $R_2$ is phenyl and $R_3$ is 4-(2-carboxy-ethyl)-phenyl, that is, 2-methoxy-2-phenyl-4[4-2-carboxy-ethyl)-phenyl]-3(2H)-furanone.

Because it is the ability of the furanone reagents to penetrate into the skin, and their fluorogenic ability to become fluorescent after covalently bonding to amine groups that is necessary to this invention, it is apparent that other reagents will be equivalent to those specifically distinguished in this disclosure. Contemplated equivalents of the furanone compounds employed in the compositions of this invention are other non-fluorescing compounds that become fluorescent after covalently bonding to proteins such as are present in the human epidermis or the outer layers of other organs. Because the compounds' fluorogenic activity, rather than an exact chemical structure, is critical to this invention, it will be apparent to those skilled in the art that other fluorogenic reagents can meet the criteria listed hereinabove.

An important advantage that the compositions of this invention have over the prior art is that they do not require an acetate component, which seals the skin, in order to enhance the mark's permanence. The discomfort to the patient and other drawbacks previously discussed are thereby avoided. A further and unexpected advantage of this invention is that because of the fluorogenic reagents' selective and relatively permanent bonding, they are effective at levels as low as 0.35% by weight (10 mM), rather than the concentrations of 7–9% by weight required in U.S. Pat. No.3,640,889.

PREPARATION AND USE

The compositions of this invention can be prepared by dissolving a furanone compound as defined above in an appropriate carrier fluid, such as, ethanol, isopropanol or dimethylsulfoxide. For example, dissolve by stirring 1 to 10 g, preferably 2 to 3 g, of such a furanone, preferably fluorescamine (commercially available from Hoffmann-LaRoche, Inc., under the trade name FLURAM TM), in 1,000 ml of the selected carrier liquid, preferably anhydrous to ethanol. Other fluorogenic reagents which may similarly be prepared in like concentrations as skin-marking compositions are those fluorogenic compounds previously described.

The marking composition can be prepared by combining and mixing the ingredients in any order which yields a normally liquid, that is liquid under ambient conditions, solution. Thus, for example, formulation can be carried out at room temperature by first dissolving the fluorogenic agent in a portion of the organic solvent, then adding the other appropriate solvents, as discussed above, if desired.

The compositions of this invention preferably also contain a visible, washable dyestuff or pigment for temporary skin marking purposes. This will permit the person marking skin to identify the areas marked, since the skin does not immediately become fluorescent under ultraviolet light. Such dyes are known as fugitive dyestuffs or pigments. They are preferably present in a concentration range of 5 to 20%, and most preferably 10 to 15%.

The skin-marking compositions of this invention can be applied with a cotton-tipped applicator or a felt-tipped marking pen. Other techniques and applicators which may be used to apply these compositions are those commonly used in the pharmaceutical arts. Any residual carrier fluid and the fugitive dyestuff can be removed from the skin by washing with soap and water, after about 30 minutes, when the furanone has reacted with the skin. Thickening agents, such as glycerol or propylene glycol can also be added to the compositions as desired.

Figure 2A:
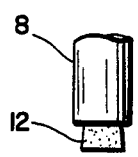
FIGS. 2a and 2b show various marking tips for the marking pen shown in FIG. 1.
Figure 2B:
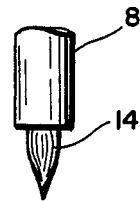

As shown in FIG. 1, a marking pen may also be utilized to apply these compositions to the skin. Such pens are well known generally and may have, for example, a housing 2 which contains a reservoir to hold the marking composition 4 (visible through the cut-away portion of the housing. A marking tip 6 extends outwardly from the tapered end 8 of housing 2 and inwardly into communication with the fluid reservoir. A removable plug 10 may be included at the end of housing 2 to fill the fluid reservoir. Neither the exact structure of the pen, nor the relative sizes and shapes of its components is essential to the operation of the marking device. Other sizes and shapes of marking tips are shown in FIGS. 2a–b. Tip 12 (FIG. 2a) is broader and thicker than tip 6, and therefore may be more useful when a large skin area must be marked. Tip 14 (FIG. 2b) shows a paint-brush type tip, which can be dipped into a vial or other container of the marking composition and the composition painted onto the appropriate skin surface. Variations and equivalents to these structures are apparent. The pen may be manufactured to accommodate interchangeable tips. Tips may be constructed of felt, or plastic, or other functional equivalents shown in the marking pen art.

From the foregoing description, one skilled in the art can easily ascertain the essential characteristics of this invention, and without departing from the spirit and scope thereof, can make various changes and modifications of the invention to adapt it to various usages and conditions. The following preferred specific embodiments are, therefore, to be construed as merely illustrative and not limitative of the disclosure in anyway whatsoever.

EXAMPLE 1

To prepare a skin-marking composition to use for indicating an area of skin for radiaton therapy, dissolve 3.4 g of fluorescamine in 1,000 ml of isopropanol. This composition may be used as the marking fluid for a marking-type pen, e.g., as shown in FIG. 1, or applied to skin with a cotton-tipped applicator.

EXAMPLE 2

A skin-marking composition is prepared by stirring 5.2 g of 4-phenylspiro[furan-2(3H),1'-phthalan]-3,3'dione in 500 ml of 95% ethanol, until it dissolves.

EXAMPLE 3

Follow the procedure of Example 1, employing 500 ml of dimethylsulfoxide or dimethylformamide.

EXAMPLE 4

Mix 500 ml of a composition of Example 1, 2 or 3 with a non-reactive fugitive dyestuff or pigment, e.g., 25 ml of conventional washable blue writing ink or green vegetable dye, thereby producing a skin marking composition which produces a mark on skin that is visible under ordinary light until the skin is washed and, after 15–30 minutes, which is visible under ultraviolet light for 2–3 weeks, even after repeated washing of the skin.

EXAMPLE 5

A felt tip pen as shown in FIG. 1 is filled through the removeable plug 10 of the non-marking end of the housing 2 with a solution as prepared in Example 1, 2, 3 or 4. The pen is then kept capped, to avoid evaporation, until needed to mark the skin of a cancer patient to indicate the site for radiation therapy, or to mark areas of a skin to which allergens are to be applied for allergy diagnostic purposes.

EXAMPLE 6

To mark the skin of a cancer patient at a site which requires a course of radiation therapy, apply a line of the marking composition as prepared in Example 1, 2, 3 or 4 around the periphery of the epidermis to be irradiated using a cotton-tipped applicator, and allow the carrier fluid to evaporate to dryness. After about 20 minutes, the area of the skin so marked can be perceived upon illumination with ultraviolet light, for a period of about 2–3 weeks.

EXAMPLE 7

The periphery of a skin lesion can be monitored as to progressive changes in size and shape by marking a line around its periphery with a composition of Example 1, 2, or 3, and then illuminating the site thus marked at periodic intervals to compare the previous extent of the lesion with that extent then-existing. The area marked will not be visible under ordinary light, but will fluoresce strongly under ultraviolet light.

EXAMPLE 8

The skin of experimental animals, such as mice or rabbits, can be marked by applying to their skins a fluorogenic composition of Example 1, 2, 3, or 4. The skin area so marked can be visualized upon its illumination with ultraviolet light. For unusually horny-skinned animals, a fluorogenic reagent in the dimethylsulfoxide carrier fluid of Example 3 is preferably employed. This causes a deeper penetration of the reagent into the skin, and thereby carries a greater quantity of reagent into the epidermis.

EXAMPLE 9

To prepare a solution for marking paper money or consumer goods such as radios, or other objects, and subsequently determining whether a given human has come into contact with the object, first coat the object with the composition prepared as follows: add 34 g of 4-(4-methoxyphenyl)spiro[furan-2(3H), 1'-phthalan]-3,3'-dione to a solvent mixture of 80 g of N-methyl pyrrolidine and 10 g of 2-aminoethanol; then add 1000 g of a commercially available alkyd resin, produced from phthalic anhydride, diethylene glycol, azelaic acid and double A castor oil which is dissolved in 2000 g of xylene. A fine suspension of the fluorogenic reagent is obtained which can be sprayed onto the subject to be marked. This composition will adhere to the object, and resist inclement weather. When the hands of persons thought to have handled the object are observed under ultraviolet light, the hands of any such person who has contacted the treated object within the last 2–3 weeks will fluoresce intensely.

EXAMPLE 10

A research animal, such as the mouse or rat that is being used in an experimental study to monitor the course of a dermal immunological reaction, is marked with a fluorogenic composition contained in the marking pen of Example 5, along the periphery of the wheal produced by subcutaneous injection of an immunogen. The periphery of the wheal is re-marked at periodic intervals during the test. As the completion of each test, the injection area is illuminated with ultraviolet light and a photograph is taken thus recording the serial extents of the immune-response area. The several areas bounded by the fluorescent outlines can be measured so as to quantify the degree of the immune reaction with respect to its time course.

EXAMPLE 11

The marking composition of Example 1, 2, or 3 is sprayed, using a conventional atomizer-type device, onto U.S. dollar bills of various denominations, and allowed to evaporate to leave an invisible residue of the fluorogenic agent, which will be transferred to the hands of a person who handles the money so marked. The presence of the fluorogenic reagent is then perceived on the hands of persons who have handled the money within the last 2–3 weeks upon illumination of their hands with ultraviolet light.

EXAMPLE 12

A solution of 0.5% fluorescamine in 100% dimethylsulfoxide was applied as a line outlining the ring worm infection sites of a human patient. During the course of therapy, the sites were illuminated with ultraviolet light in order to produce an intensely fluorescent zone that was compared with the extent of the infection then present in order to compare the efficacies of several medications.

EXAMPLE 13–17

Follow the procedure of Examples 6, 7, 8, 10 and 12, employing a marking composition of Example 4. This allows the area to which the marking composition is applied to be visualized under ordinary light during the application of the marking composition. This fugitive dye can be removed by gentle washing after about one-half hour, or longer, after application, when reaction of the fluorogenic agent is complete.

What is claimed is:

1. In a diagnostic or therapeutic procedure repeatedly involving a same area of the skin, which occurs at intervals of from 1 to about 21 days and wherein an area of the skin of a patient is marked to delineate the area of the skin involved in the procedure, the improvement comprising marking the skin with a fluorogenically-effective amount, in a carrier liquid, of a furanone of the formula

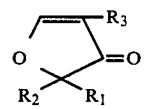

wherein $R^1$ is lower alkoxy or phenyl lower alkoxy and $R_2$ is

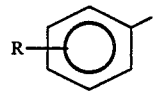

or, $R_1$ and $R_2$ collectively are

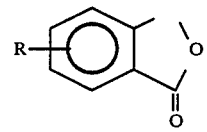

wherein R in each instance is hydrogen or one or more of halogen, lower alkyl, trifluoromethyl, lower alkoxy, nitrol, cyano, carboxy or carboxy lower alkyl, and $R_3$ is lower alkyl, phenyl lower alkyl or aryl, thereby rendering the marked area visible under ultraviolet light after about 15–30 minutes and thereafter identifying the marked area by examination of the skin under ultraviolet light, whereby the patient may wash the marked area and avoid the embarrassment of visibly marked skin during the time period between procedures.

2. A method according to claim 1, wherein the furanone is fluorescamine.

3. A method according to claim 1, wherein the skin is simultaneously marked with a visibly-effective fugitive dye or pigment which is readily removeable by washing.

4. A method according to claim 3, wherein the furanone is fluorescamine.

* * * * *